United States Patent
Nicholes et al.

(10) Patent No.: US 6,783,429 B2
(45) Date of Patent: Aug. 31, 2004

(54) APPARATUS AND METHOD FOR SAMPLING A CHEMICAL-MECHANICAL POLISHING SLURRY

(75) Inventors: Mary Kristin Nicholes, Eden Prairie, MN (US); Stephen John Carlson, Shorewood, MN (US); Mark R. Litchy, Plymouth, MN (US)

(73) Assignee: The BOC Group, Inc., Murray Hill, NJ (US)

( * ) Notice: Subject to any disclaimer, the term of this patent is extended or adjusted under 35 U.S.C. 154(b) by 144 days.

(21) Appl. No.: 10/215,774

(22) Filed: Aug. 9, 2002

(65) Prior Publication Data

US 2003/0076495 A1 Apr. 24, 2003

Related U.S. Application Data

(60) Provisional application No. 60/313,442, filed on Aug. 17, 2001.

(51) Int. Cl.[7] .................................................. B24B 1/00
(52) U.S. Cl. ............................. 451/6; 451/36; 451/60; 451/446; 137/888; 137/894
(58) Field of Search ........................... 451/6, 8, 36, 41, 451/60, 446; 137/2, 814, 825, 572, 894, 897, 898, 888; 222/1, 61

(56) References Cited

U.S. PATENT DOCUMENTS

| | | | | |
|---|---|---|---|---|
| 6,019,250 A | * | 2/2000 | Pozniak et al. | 222/1 |
| 6,077,147 A | * | 6/2000 | Yang et al. | 451/6 |
| 6,149,508 A | * | 11/2000 | Vanell et al. | 451/72 |
| 6,168,048 B1 | * | 1/2001 | Xu et al. | 222/1 |
| 6,183,352 B1 | * | 2/2001 | Kurisawa | 451/87 |
| 6,270,246 B1 | * | 8/2001 | Han | 366/131 |
| 6,616,014 B1 | * | 9/2003 | Provost et al. | 222/129.3 |
| 6,652,366 B2 | * | 11/2003 | Dyer | 451/60 |

* cited by examiner

Primary Examiner—Eileen P. Morgan
(74) Attorney, Agent, or Firm—Ira Lee Zebrak

(57) ABSTRACT

An apparatus and method for drawing a sample of a chemical-mechanical polishing slurry for analysis of at least one property, e.g., particle size distribution, is described. The apparatus comprises (i) a plurality of sample delivery lines, each line carrying a chemical-mechanical polishing slurry, (ii) a manifold in fluid communication with the plurality of sample delivery lines, (iii) means for opening and closing the fluid communication between each sample delivery line and the manifold, (iv) an aspirator in fluid communication with the manifold, (vi) means opening and closing the fluid communication between the aspirator and the manifold, (vii) a pressure between the aspirator and the sample delivery lines, a reduction in the pressure resulting in the draw of a sample from the sample delivery line into the manifold when the fluid communication between the line and the manifold is open, (viii) a sensor for measuring the at least one property of the slurry, the sensor in fluid communication with the manifold, and (ix) means for opening and closing the fluid communication between the manifold and the sensor.

12 Claims, 4 Drawing Sheets

FIG. 3

APPARATUS AND METHOD FOR SAMPLING A CHEMICAL-MECHANICAL POLISHING SLURRY

CROSS-REFERENCE TO RELATED APPLICATIONS

Priority is claimed to U.S. provisional patent application Serial No. 60/313,442 filed on Aug. 17, 2001.

BACKGROUND OF THE INVENTION

1. Field of the Invention

The invention relates to sampling chemical-mechanical polishing slurries. In one aspect, the invention relates to sampling such slurries to monitor one or more properties of the slurry while in another aspect, the invention relates to using an aspirator to draw the slurry into a liquid sampling system.

2. Description of the Related Art

A chemical-mechanical polishing (CMP) system is often employed in the microelectronics industry to contour and/or polish semiconductor wafers. These systems typically contain and employ a "slurry" which is cycled throughout the system such that the slurry contacts and/or impinges upon the wafers. As the cycling slurry impacts and/or passes over the wafers, the wafers are contoured and polished.

In order to maintain the consistency, performance, efficiency, and/or usefulness of the system, the "health" of the slurry must be maintained. Slurry instability, external contamination, or process conditions (e.g., shear-inducing pressure gradients, flow rates, and exposure to air) may all compromise slurry health. Thus, slurry properties (e.g., specific gravity, pH, weight percent solids, ionic contamination level, zeta potential, and particle size distribution (PSD)), are often closely monitored by sampling systems.

Of all the slurry health properties, perhaps the most important and frequently monitored is PSD. In the industry, PSD can be observed using a variety of instruments such as sensors, analyzers, and like devices (collectively referred to as sensors) that are commercially available from a host of manufacturers. For example, one such sensor is the Accu-Sizer 780/OL (AccuSizer) manufactured by Particle Sizing Systems (PSS) of Santa Barbara, Calif.

Unfortunately, while these PSD sensors are generally suitable for analyzing slurry, these sensors can possess disadvantages in some circumstances. Certain of these sensors are generally limited to sampling a single slurry at a single sampling point (i.e., a location within a CMP system from where a sample is taken). In other words, each CMP system, as well as each slurry used within that CMP system, would require a dedicated sensor. Since integrated circuit manufacturers, as well as others, often desire to analyze numerous different slurries, from multiple sampling points (i.e., locations), a one-to-one ratio of sensor to slurry would dramatically increases costs. Therefore, a liquid sampling system, using a single sensor, capable of monitoring one of a plurality of slurries from multiple sampling points was developed.

The liquid sampling system was built around a sensor to permit measurement of a number of different slurries, from multiple sample points, by utilizing a multi-port valve manifold. The multi-port valve manifold is operable, within the liquid sampling system, to selectively route any one of a number of different slurries, from a variety of locations, to a single sensor for PSD analysis.

While developing, testing and using the liquid sampling system, the need to repeatedly draw and/or introduce the slurry into the liquid sampling system became apparent. The slurries could, and often were, provided by one of many independent slurry supply lines. Therefore, in order to draw slurry into the liquid sampling system, a pump or like device would need to be associated with every slurry supply line. In other words, a one-to-one ratio of slurry supply lines to pumps would be required.

Unfortunately, the use of multiple pumps within the liquid sampling system presented numerous drawbacks and disadvantages. Specifically, the cost of purchasing, maintaining, and operating numerous pumps posed a significant financial burden. The pumps can be expensive, can be subject to mechanical difficulties that lead to down-time, and can voraciously consume energy. Further, the pumps can occupy valuable space within the liquid sampling system and, therefore, render the liquid sampling system cumbersome. Thus, an apparatus and method capable of drawing a liquid into a liquid sampling system without the use of multiple pumps or other multiple drawing apparatus are desirable.

SUMMARY OF THE INVENTION

In one aspect, the invention is a method of drawing a liquid sample into a liquid sampling system from at least one of a plurality of liquid delivery lines, the liquid sampling system comprising (i) a multi-valve manifold in fluid communication with the liquid delivery lines, (ii) an aspirator in fluid communication with the manifold, and (iii) a pressure between the aspirator and the liquid delivery lines, the method comprising:

activating the aspirator to reduce the pressure in the manifold relative to the liquid delivery lines; and activating at least one valve on the manifold to selectively draw into the manifold a liquid sample from at least one liquid delivery line.

The aspirator is activated by passing a fluid, e.g., water, through it, and the liquid sample is typically a chemical-mechanical polishing slurry.

In another embodiment, the invention is an apparatus for drawing a sample of a chemical-mechanical polishing slurry for analysis of at least one property, the apparatus comprising (i) a plurality of sample delivery lines, each line carrying a chemical-mechanical polishing slurry, (ii) a manifold in fluid communication with the plurality of sample delivery lines, (iii) means for opening and closing the fluid communication between each sample delivery line and the manifold, (iv) an aspirator in fluid communication with the manifold, (vi) means opening and closing the fluid communication between the aspirator and the manifold, (vii) a pressure between the aspirator and the sample delivery lines, a reduction in the pressure resulting in the draw of a sample from the sample delivery line into the manifold when the fluid communication between the line and the manifold is open, (viii) a sensor for measuring the at least one property of the slurry, the sensor in fluid communication with the manifold, and (ix) means for opening and closing the fluid communication between the manifold and the sensor.

The means for opening and closing the fluid communication between the manifold and the sample delivery lines, aspirator and sensor is typically at least one valve. The sensor can vary to convenience, e.g., an optical particle counter.

BRIEF DESCRIPTION OF THE DRAWINGS

Embodiments of the invention are disclosed with reference to the accompanying drawings and are for illustrative purposes only. The invention is not limited in its application

DETAILED DESCRIPTION OF THE PREFERRED EMBODIMENTS

Various items of equipment, such as fittings, valves, mountings, pipes, sensors, monitoring equipment, wiring, and the like have been omitted to simplify the description. However, such conventional equipment and its uses are known to those skilled in the art and can be employed as desired. Moreover, although the invention is described below in the context of slurries used in chemical-mechanical polishing processes, those skilled in the art will recognize that the invention can be employed with, and has applicability to, many other and different processes.

Figure 1:
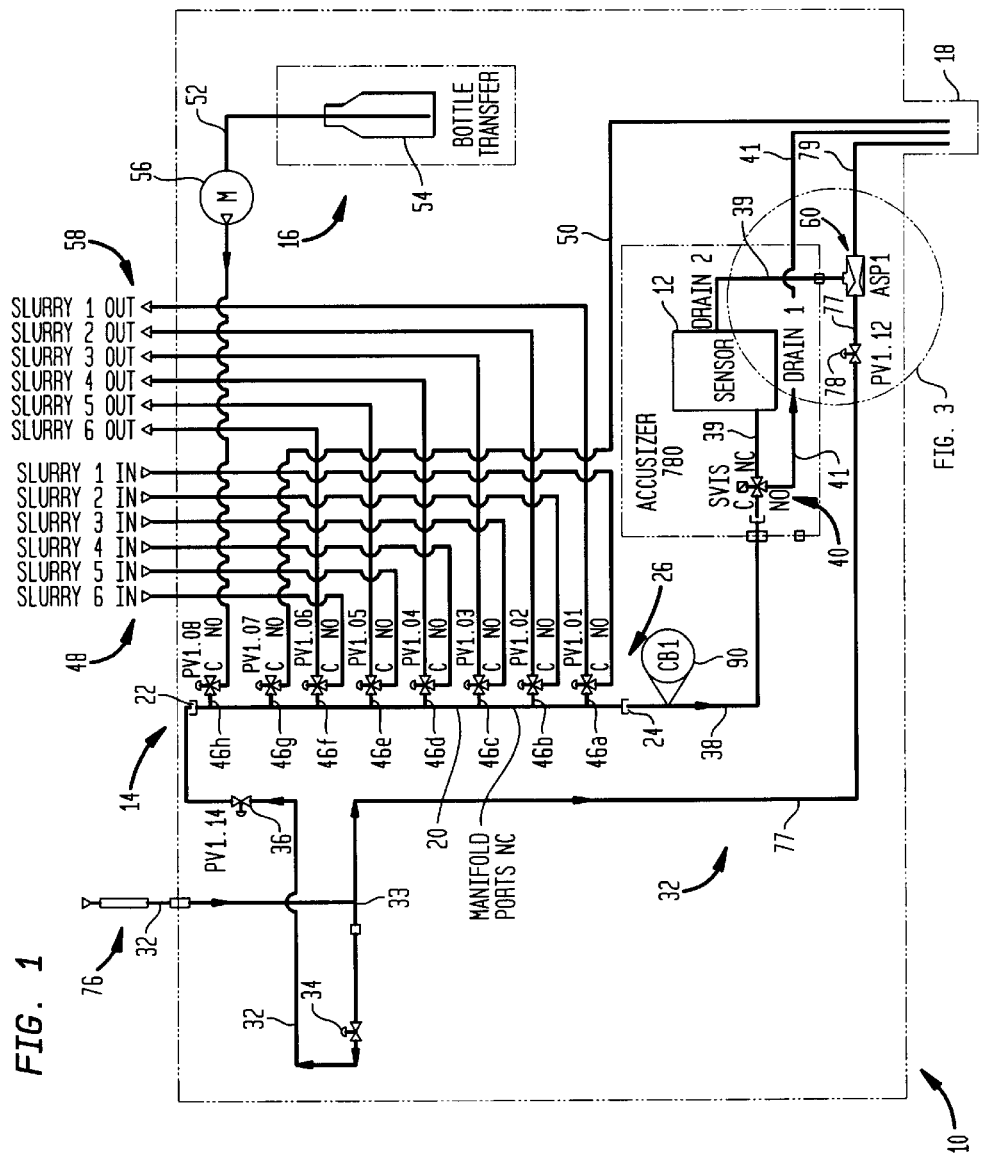
FIG. 1 is a schematic representation of a liquid sampling system comprising one embodiment of an aspirator in accordance with one aspect of the present invention.

Referring to FIG. 1, a schematic representation of a liquid sampling system 10 is illustrated. In preferred embodiments, system 10 comprises a liquid sampling system known as the intelligent Slurry Particle Equipment (iSPEQ) system. The iSPEQ system is operable to monitor the health of chemical-mechanical polishing slurries. An exemplary description of the iSPEQ system is provided in commonly-owned, co-pending U.S. patent application Ser. No. 10/215,799 filed Aug. 9, 2002, entitled "Sampling and Measurement System with Multiple Slurry Chemical Manifold", and the contents and disclosure of that application are incorporated into the present application by this reference as if fully set forth herein.

System 10 comprises sensor 12, multi-port valve manifold 14, bottle sample station 16, system drain 18, and aspirator 60. System 10 is operable to monitor and/or analyze a collected sample of slurry (or other liquid), that has been selectively and/or sequentially provided to the system. One example of slurry suitable for testing in system 10, and commonly used in CMP systems, is Semi-Sperse SS-12 manufactured by Cabot Corporation, Boston, Mass. When operating system 10 slurry can be obtained from any number of sampling points (e.g., locations) within a single CMP system (not shown) and/or within several CMP systems. Also, slurry can be taken at any time during the "life" (i.e., period of use in a CMP system and/or systems) of the slurry.

For system 10 to monitor and/or analyze a slurry sample, the system relies on sensor 12. Sensor 12, as schematically illustrated in FIG. 1, comprises any sensor capable of monitoring and/or analyzing the health, and particularly the PSD, of slurry. Sensors that can be used in the practice of this invention are available from a host of different manufacturers, e.g., the AccuSizer 780/OL or the NICOMP 380/ZLS from Particle Sizing Systems (PSS) of Santa Barbara, Calif.; the LSTM 230 from Beckman Coulter of Fullerton, Calif.; the Lab CMP Slurry Monitor from Colloidal Dynamics of New South Wales, Australia; and the Liquilaz-SO5 or the SlurryChek from Particle Measuring Systems of Boulder, Colo. This list of acceptable and capable sensors, while certainly illustrative, is not intended to be exhaustive.

Although all of these sensors possess the ability to more than adequately monitor PSD, they can be fundamentally different in their manner of operation. Therefore, depending on the circumstances and manner of use, one sensor can be preferred over another for a given application. In certain embodiments of system 10, the AccuSizer 780/OL is a preferred sensor. The AccuSizer, a single optical particle counter, is described in detail in U.S. Pat. No. 5,835,211 (Wells, et. al.), and it is incorporated into the present application by this reference as if fully set forth herein.

Figure 2:
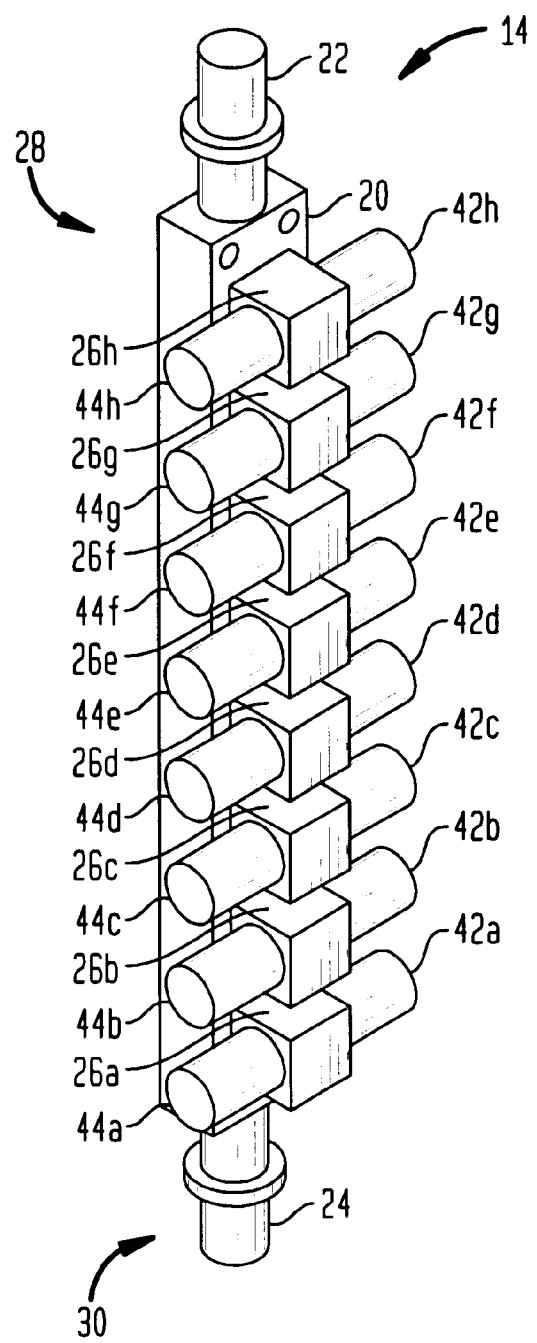
FIG. 2 is a perspective view of a valve manifold employed within the liquid sampling system of FIG. 1.

Referring now to both FIGS. 1 and 2, multi-port valve manifold 14 comprises manifold body 20, manifold intake 22, manifold outlet 24, and a plurality of multi-port valves 26a–h (collectively 26). As shown in FIG. 2, manifold 14 has a top 28 and a bottom 30. In a preferred embodiment, manifold 14 is "vertically oriented" such that top 28 is vertically disposed above bottom 30 when the manifold is incorporated and/or employed within system 10. When manifold 14 is vertically oriented, manifold intake 22 is proximate top 28 and manifold outlet 24 is proximate bottom 30. As described in more detail below, flushing of manifold 14 is often enhanced when manifold 14 is vertically oriented. The pressure within manifold 14 will vary over the operation of the sampling system particularly during flushing (e.g., rinsing) operations.

Manifold body 20 comprises a structural member (e.g., a tube, a pipe, a channel, or the like) that has and defines internal surfaces or walls (not shown). Manifold body 20 is capable of permitting various fluids (e.g., liquids, gases, slurries, etc.) to flow and/or pass through it.

Manifold intake 22 and manifold outlet 24 are connected to manifold body 20 proximate top 28 and bottom 30, respectfully, (i.e., at opposing ends) of manifold 14. Manifold intake 22 can deliver flushing liquid into manifold body 20 by receiving the liquid from supply line 32. The flushing liquid flows from and through supply line 32 to dividing point 33. At dividing point 33, the flushing liquid can be divided into two steams such that at least a portion of the flushing liquid flows through pressure valves 34 and 36, through manifold intake 22, and into manifold body 20 and manifold 14. Manifold outlet 24 expels flushing liquid and other substances from manifold body 20 and manifold 14. Therefore, the flushing liquid can pass through manifold 14, and preferably, capture those other substances remaining in the manifold. The flushing liquid, as well as other substances, are then discharged through manifold outlet 24 into manifold discharge line 38, through safety valve 40, and passed to either sensor line 39 or drain line 41. As such, the flushing liquid and other substances are either delivered to sensor 12 or system drain 18.

Although manifold 14 as shown in FIGS. 1 and 2 is equipped with eight multi-port valves 26 (e.g., three-way valves), any number of the multi-port valves can be used. In an exemplary embodiment, a pneumatic, eight-port, three-way valve manifold from Saint-Gobain Performance Plastic of Wayne, N.J. (formerly Furon Company) may be suitably employed as manifold 14. In the embodiment of FIG. 2, each of multi-port valves 26a–h comprises an intake port 42a–h (collectively 42), an outlet port 44a–h (collectively 44), and a body port 46a–h (collectively 46) (schematically shown in FIG. 1).

Referring to FIG. 1, intake ports 42a–h can be connected as desired to either a slurry supply line 48, a drain line 50, or a bottle sample line 52. In a preferred embodiment, intake ports 42a–f are each associated with a slurry supply line 48 and, therefore, can receive slurry from one of the respective slurry supply lines when the intake port is actuated or open. Thus, various samples of slurry can, in preferred embodiments, be selectively received into manifold 14 through one of intake ports 42a–f within valves 26a–f.

Intake ports 42g–h can be connected as desired to either drain line 50 or bottle sample line 52. In a preferred embodiment, as shown in FIG. 1, intake port 42g actually functions as an outlet (despite being labeled as an intake port). Thus, if necessary or desired, intake ports can be employed as outlet ports, and vise versa. Although illustrated in FIG. 1 as unconnected and/or unused, outlet ports 44g–h can be, if desired, connected to drain line 50 and bottle sample line 52, respectively, in lieu of the lines being connect to intake ports 42g–h.

Intake port 42g, in one embodiment, is associated with drain line 50, and can, therefore, permit the discharge of air, gas pockets, flushing liquid, slurry, and other substances from manifold 14 when the intake port is actuated or open. As such, intake port 42g can, and often does, operate as a vent for manifold 14. When operating as a vent, intake port 42g is typically located proximate top 28 of manifold 14.

Intake port 42h, in one embodiment, is associated with bottle sample line 50, and can, therefore, receive slurry from bottle transfer station 16 when the intake port is actuated or open. Bottle transport station 16 permits a sample of slurry from a remote location and/or unconnected CMP system to nonetheless be introduced into manifold 14 and, consequently, to sensor 12. In other words, slurry from bottle transfer station 16 can be selectively introduced into manifold 14.

Bottle sample station 16 comprises bottle 54 and pump 56. Pump 56 can be operated to draw slurry from bottle 54 such that a slurry sample can be delivered, through slurry sample line 52, to manifold 14. The delivered slurry sample from sample line 52 can be received by intake port 42h of valve 26h. In an alternative embodiment, an aspirator or other device capable of transporting a fluid (e.g., flushing liquid, slurry, nitrogen gas, and the like) may be substituted for pump 54.

Referring again to FIG. 1, outlet ports 44a–f are each associated with a slurry discharge line 58 and, therefore, can discharge slurry through one of the respective slurry discharge lines 58 when the outlet ports are actuated or open. Thus, various samples of slurry can be selectively expelled from manifold 14 through one of outlet ports 44a–f within valves 26a–f. In preferred embodiments, slurry is substantially continuously flowed from each slurry supply line 48 into an associated valve 26 and then discharged from the valve through an associated respective discharge line 58. As such, the slurry is not permitted to settle and/or precipitate in valves 26 and slurry lines 48, 58.

Each body port 46a–h is integral or secured to, and associated with, manifold body 20. As such, each valve 26 is provided with a conduit (e.g., corridor) to manifold body 20. Therefore, when body ports 46 are actuated or open, any ultra pure water entering manifold 14 through manifold intake 22 can enter into each of valves 26 and, likewise, any slurry entering manifold 14 through one of intake ports 42a–f can enter into manifold body 20. In other words, valves 26 and manifold body 20 are in fluid communication with each other. Therefore, as shown in FIG. 1, slurry can be discharged from manifold 14 through manifold outlet 24 and/or through one of outlet ports 44a–f, as desired.

Should slurry be expelled from manifold 14 through manifold outlet 24, the slurry can travel through discharge line 38 until encountering safety valve 40. During sampling and monitoring of slurry, safety valve 40 can be actuated or open to direct the slurry through sensor line 39 such that the slurry flows into, or proximate, sensor 12. As such, slurry can be monitored and/or analyzed by sensor 12. However, during rinsing, flushing, and pulsing, safety valve 40 can be actuated or open to direct slurry through drain line 41 where the slurry can be discharged from system 10 through system drain 18.

Prior to this invention, slurries were typically moved throughout slurry lines by employing, for example, one or more pumps. The pumps in conventional systems are selectively operated to push or pull the slurry through the system such that the slurry is transported from a source to a desired locale. However, the use of pumps can be expensive and impractical, especially when slurry is made available from more than one source. Therefore, instead of system 10 employing numerous, expensive, and maintenance-prone pumps, the system utilizes aspirator 60 to transport slurry from plurality of slurry lines 48.

Figure 3:
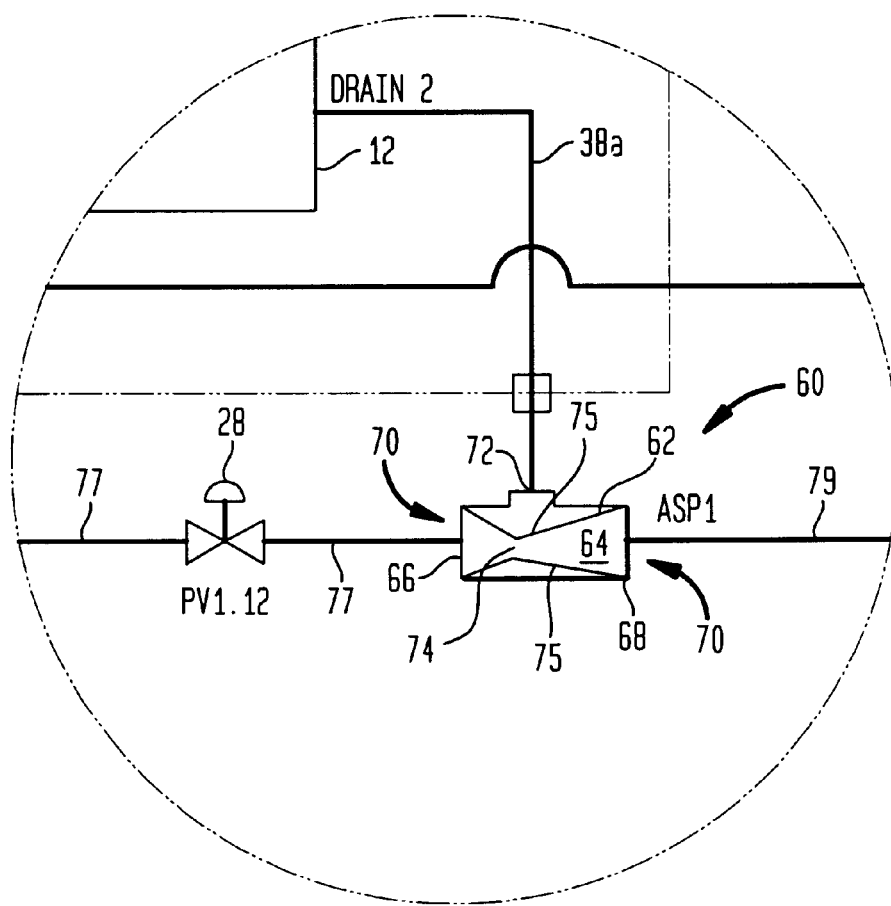
FIG. 3 is a more detailed schematic representation of the aspirator of FIG. 1.

Turning to FIG. 3, aspirator 60 comprises an aspirator body 62 (e.g., an elongate tube, a cylinder, and the like) defining a channel 64 within and through the aspirator, an aspirator intake 66 and an aspirator outlet 68 at opposing ends 70 of the aspirator body, and an aspirator suction port 72 disposed between the aspirator intake and the aspirator outlet and proximate a constricted portion 74 of the channel. Baffles 75 or like devices, as well as aspirator body 62, can used and/or configured to form the constricted portion 74 of channel 64 within aspirator body 62.

Supply line 32 includes an upstream line 77 and a downstream line 79. Upstream line 77 extends from aspirator 60 to dividing point 33 and from dividing point 33 to fluid source 76. Upstream line does not, however, include that portion of supply line 32 that extends from dividing point 33, passed valve 34, and on to manifold inlet 22. Downstream line 79 extends between aspirator 60 and system drain 18. When aspirating fluid is delivered by fluid source 76, the aspirating fluid can flow through both upstream and downstream lines 77, 79 such that the aspirating fluid travels from the fluid source to system drain 18.

In a preferred embodiment, upstream line 77 includes fluid supply valve 78. Fluid supply valve 78 can be selectively actuated to permit or deny the aspirating fluid to flow from upstream line 77 to downstream line 79. Therefore, fluid supply valve 78 can control the flow of aspirating fluid through aspirator 60.

In a preferred embodiment as shown in FIGS. 1 and 3, upstream line 77 is secured to aspirator intake 66 and downstream line 79 is secured to aspirator outlet 68. Therefore, aspirating fluid travelling through fluid supply line 32 is permitted to flow through channel 64 within aspirator body 62 of aspirator 60.

Suction port 72 of aspirator 60 is preferably secured to sensor line 39. As such, suction port 72 is in fluid communication with sensor 12, discharge line 38, sensor line 39, manifold 14, and the plurality of slurry supply lines 48. Thus, slurry can be provided by one of slurry supply lines 48, enter manifold 14, travel through manifold discharge line 38, sensor line 39, pass through or by sensor 12, and arrive at suction port 72 of aspirator 60.

Upon reaching suction port 72, slurry can pass into aspirator body 60, enter channel 64, and combine and/or mix with the aspirating fluid flowing through the channel.

Thereafter, the slurry or mix of slurry and aspirating fluid can be expelled from aspirator 60 at aspirator outlet 68, pass through downstream line 79, and be removed from system 10 by system drain 18.

Figure 4:
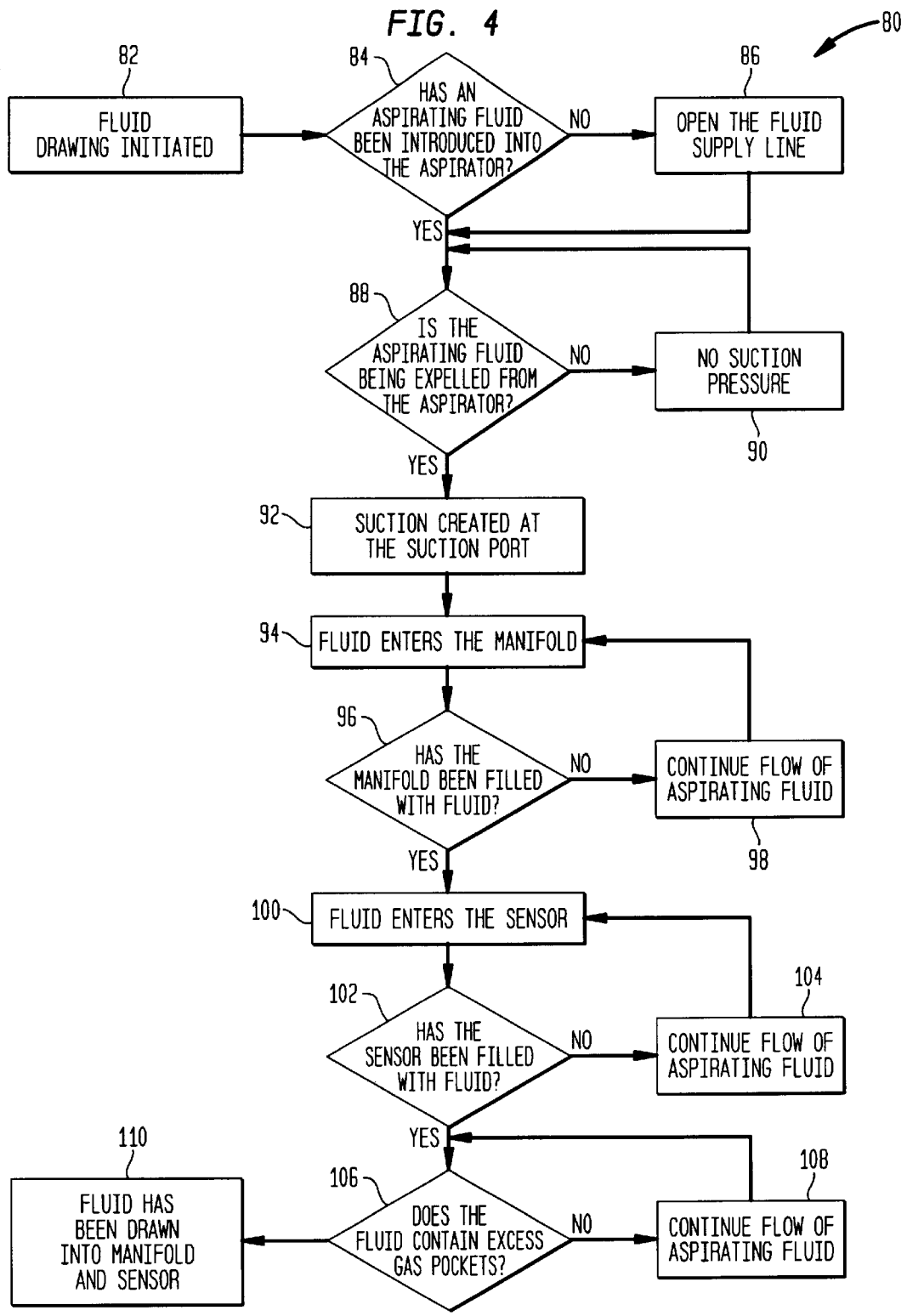
FIG. 4 is a flowchart outlining the steps for drawing a fluid into the fluid sampling system with the aspirator of FIGS. 1 and 3.

In operation, as illustrated in FIG. 4, a procedure 80 for drawing fluid (e.g., a slurry) into system 10, and particularly manifold 14 and sensor 12, is outlined. When procedure 80 for drawing the fluid is initiated 82, a determination 84 of whether an aspirating fluid (e.g., ultra pure water) has been introduced into aspirator 60 is made. If the aspirating fluid has not been introduced, fluid supply line 32 (FIG. 1) is opened 86 by actuating fluid supply valve 78 (FIG. 1). With fluid supply valve 78 opened, the aspirating fluid is introduced into, flows through, and is discharged from aspirator 60.

After the aspirating fluid has been introduced into aspirator 60, a determination 88 of whether the aspirating fluid is expelled from aspirator 60 is made. If no aspirating fluid is expelled, a vacuum, partial vacuum, negative pressure, reduced pressure, and/or suction (collectively "suction") is not produced, created, and/or generated 90 at suction port 72. However, if the aspirating fluid is expelled, suction is produced 92 at suction port 72 and can be used to draw fluid.

Suction created 92 at suction port 72 preferably draws, pulls, and/or biases a selected fluid from one of fluid delivery lines 48. To draw the selected fluid, manifold 14 is operated such that one of intake ports 42*a–f* within one of multi-port valves 26 is opened. When this occurs, the selected fluid can be drawn from within the corresponding fluid delivery line 48 such that the fluid begins to fill 94 manifold 14.

As the selected fluid continues filling manifold 14, a determination 96 as to whether the manifold has been filled with the fluid is made. If manifold 14 has not been substantially or at least partially filled with the drawn fluid, the flow of aspirating fluid (i.e., introduction and expulsion of the aspirating fluid into, through, and from aspirator 60) is maintained. In other words, the creation of suction is perpetuated and the fluid continues 98 to be drawn into manifold 14. If, however, manifold 14 has been completely or partially filled with the fluid, the fluid can discharge from the manifold at manifold outlet 24. Fluid discharged from manifold outlet 24 travels through manifold line 38 (FIG. 1) and arrives at, and enters, sensor 12.

Since sensor 12 can be considerably more delicate and fragile than manifold 14, the rate at which the fluid is drawn into and through sensor 12 is often reduced in comparison to the rate at which fluid is drawn into manifold 14. This is accomplished by reducing the rate (e.g., velocity) of aspirating fluid passing through aspirator 60. When the velocity of aspirating fluid is reduced, a weaker and/or smaller suction is produced at suction port 72. The weaker suction causes the velocity of the drawn fluid to decrease. The decreased velocity of the drawn fluid permits sensor 12 to be filled slower than manifold 14. As such, sensor 12 can be filled with the drawn fluid without damaging or injuring the sensor, fouling the calibration of the sensor, and the like. Of course, when the rate of fluid drawn into the sensor is slowed, the rate of fluid entering manifold 14 is correspondingly reduced.

As fluid enters sensor 12, a determination 102 whether the sensor has been filled with the drawn fluid is made. If sensor 12 has not been substantially or at least partially filled with the drawn fluid, the flow of aspirating fluid is maintained. Therefore, the creation of suction is perpetuated and the fluid continues 104 to be drawn into sensor 12. If, however, sensor 12 has been completely or partially filled with the fluid, the drawing of the fluid can be terminated. To terminate the drawing of the fluid, the flow of the aspirating fluid is discontinued by, for example, activating valve 78 and/or valve 34.

With the drawn fluid having been delivered into sensor 12, the sensor is permitted to operate. Operation of sensor 12 can provide and/or generate data or output regarding the health of the fluid, including particle size distribution. Thereafter, the fluid can, when desired, discharge from sensor 12 through drain line 41 and be expelled from system 10.

In exemplary embodiments, after sensor 12 has been at least partially filled 102 with the fluid a determination 106 whether the fluid contains excess gas pockets is made. If the fluid does contain an unacceptable level or amount of gas pockets entrained or mixed with the fluid, the flow of the aspirating fluid can be continued 108. By continuing 108 the flow of aspirating fluid, drawn fluid will continue to enter, and preferably flow through, sensor 12. As such, the drawn fluid containing the gas pockets can be expelled from sensor 12.

After sensor 12 has been filled with fluid, and possibly after gas pockets have been removed and the sensor operated, procedure 80 for drawing fluid is complete 110. In the context of system 10, procedure 80 has permitted aspirator 60 to move, transport, and/or selectively deliver a slurry from one of slurry supply lines 48.

In a preferred embodiment, a single aspirator 60 is in operational association with a multi-port valve manifold 14 within system 10. As such, single aspirator 60 and multi-port valve manifold 14 are operable, in combination, to permit a slurry to be selectively drawn from one of the plurality of supply lines 48 into the manifold, and thereafter, the sensor.

Within system 10, ultra pure water is typically employed as the aspirating and flushing liquid. However, other grades of water can also be used in various embodiments of this invention, such de-ionized water and demineralized water. Ultra pure water, as known and conventionally used in integrated circuit production facilities throughout the United States, itself is available in various grades, e.g., c-grade ultra pure water, semiconductor grade ultra pure water, and the like. The composition of ultra pure water does and can vary from producer to producer, but a common guideline for ultra pure water can be found in "Ultra Pure Water Monitoring Guidelines 2000" from Balazs Analytical Laboratory in Sunnyvale, Calif.

Gases (e.g., nitrogen, oxygen, etc.) can also be employed, if desired, as the aspirating fluid. Furthermore, aspirator 60 can draw fluids other than one or more slurries, and manifold 14 can employ a variety of valves (e.g., a two-way valve, a four-way valve, and the like) in lieu of the three-way multi-port valves 26 illustrated in FIG. 1.

Commonly-owned, co-pending U.S. patent application Ser. No. 10/215,751 entitled "Flushing A Multi-Port Valve Manifold", filed on Aug. 9, 2002, and U.S. patent application Ser. No. 60/363,933 entitled "Next Generation Sampling And Measurement System For Use With Multiple Slurry Chemical Manifold", filed on Mar. 13, 2002, disclose other and various embodiments and components within a liquid sampling system that are compatible with a chemical-mechanical polishing system and, therefore, the contents and disclosure of these applications are incorporated into the present application by reference as if fully set forth herein.

Despite any methods being outlined in a step-by-step sequence, the completion of acts or steps in a particular chronological order is not mandatory. Further, elimination, modification, rearrangement, combination, reordering, or the like, of acts or steps is contemplated and considered within the scope of the description and claims.

While the aspirating method is described in terms of a multi-port valve manifold, and more specifically a multi-port valve manifold for use within a CMP slurry sampling system, the inventors contemplate that the method is equally applicable to other system components and may have other practical applications. Furthermore, while the present invention has been described in terms of the preferred embodiment, it is recognized that equivalents, alternatives, and modifications, aside from those expressly stated, are possible and within the scope of the appending claims.

What is claimed is:

1. A method of drawing a liquid sample into a liquid sampling system from at least one of a plurality of liquid delivery lines, the liquid sampling system comprising (i) a multi-valve manifold in fluid communication with the liquid delivery lines, (ii) an aspirator in fluid communication with the manifold, and (iii) a pressure between the aspirator and the liquid delivery lines, the method comprising:

activating the aspirator to reduce the pressure in the manifold relative to the liquid delivery lines; and activating at least one valve on the manifold to selectively draw into the manifold a liquid sample from at least one liquid delivery line.

2. The method of claim 1 in which the aspirator is activated by passing an aspirating fluid through the aspirator.

3. The method of claim 1 in which the liquid sample is a chemical-mechanical polishing slurry.

4. The method of claim 3 in which the aspirating fluid is water.

5. The method of claim 4 in which the liquid sampling system further comprises a sensor for analyzing at least one property of the sample fluid, the sensor in fluid communication with the manifold.

6. The method of claim 5 in which the property analyzed by the sensor is the particle size distribution of the slurry.

7. An apparatus for drawing a sample of a chemical-mechanical polishing slurry for analysis of at least one property, the apparatus comprising (i) a plurality of sample delivery lines, each line carrying a chemical-mechanical polishing slurry, (ii) a manifold in fluid communication with the plurality of sample delivery lines, (iii) means for opening and closing the fluid communication between each sample delivery line and the manifold, (iv) an aspirator in fluid communication with the manifold, (vi) means opening and closing the fluid communication between the aspirator and the manifold, (vii) a pressure between the aspirator and the sample delivery lines, a reduction in the pressure resulting in the draw of a sample from the sample delivery line into the manifold when the fluid communication between the line and the manifold is open, (viii) a sensor for measuring the at least one property of the slurry, the sensor in fluid communication with the manifold, and (ix) means for opening and closing the fluid communication between the manifold and the sensor.

8. The apparatus of claim 7 in which the means for opening and closing the fluid communication between the manifold and the sample delivery lines is at least one valve.

9. The apparatus of claim 7 in which the means for opening and closing the fluid communication between the manifold and the aspirator is at least one valve.

10. The apparatus of claim 7 in which the means for opening and closing the fluid communication between the manifold and the sensor is at least one valve.

11. The apparatus of claim 7 in which the sensor is a single optical particle counting sensor.

12. The apparatus of claim 7 comprising a single aspirator.

* * * * *